United States Patent [19]

Balani et al.

[11] Patent Number: 5,169,769
[45] Date of Patent: Dec. 8, 1992

[54] METHOD OF HYDROXYLATING SUBSTITUTED 3-AMINOPYRIDINONES USING MAMMALIAN TISSUE

[75] Inventors: Suresh K. Balani, Hatfield, Pa.; Byron H. Arison, Watchung, N.J.; Harri G. Ramjit; Anthony D. Theoharides, both of Lansdale, Pa.; Laura R. Kauffman, Jeffersonville, Pa.

[73] Assignee: Merck & Co., Inc., Rahway, N.J.

[21] Appl. No.: 711,785

[22] Filed: Jun. 7, 1991

[51] Int. Cl.$^5$ .............................. C12P 17/14
[52] U.S. Cl. .................... 435/120; 435/118
[58] Field of Search ...................... 435/118, 120

[56] References Cited

U.S. PATENT DOCUMENTS

| | | | |
|---|---|---|---|
| 3,715,358 | 2/1973 | Witzel et al. | 260/294.8 T |
| 3,835,143 | 9/1974 | Witzel et al. | 260/294.8 T |
| 3,846,553 | 11/1974 | Shen et al. | 424/263 |

OTHER PUBLICATIONS

Krumdieck, et al., *Anal. Biochem,* vol. 104: 118 (1980).
Smith et al., *Life Sci.,* vol. 36: 1367 (1985).
Azri, et al., *In Vitro Tox.,* vol. 3: 309 (1990).
Chapman, et al., *Drug Metab and Dispos.,* vol. 18: 929 (1990).

*Primary Examiner*—David M. Naff
*Assistant Examiner*—Sandra Saucier
*Attorney, Agent, or Firm*—Charles M. Caruso; Roy D. Meredith; Carol S. Quagliato

[57] ABSTRACT

Incubation of

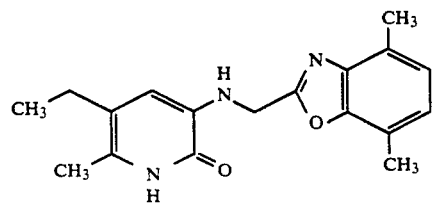

with a preparation from mammalian organ yields as biotransformation products the 6-hydroxymethyl and 5-(1-hydroxy)ethyl anologs. These products are useful in the prevention or treatment of infection by HIV and the treatment of AIDS.

5 Claims, No Drawings

METHOD OF HYDROXYLATING SUBSTITUTED 3-AMINOPYRIDINONES USING MAMMALIAN TISSUE

This application is related to copending U.S. application Ser. No. 539,643 filed on Jun. 18, 1990; Ser. No. 539,681 filed on Jun. 18, 1990; Ser. No. 539,760 filed on Jun. 18, 1990; Ser. No. 599,968 filed on Oct. 18, 1990; and Ser. No. 608,104 filed on Nov. 1, 1990.

The present invention relates to a novel process for the preparation of compounds (I) and (II)

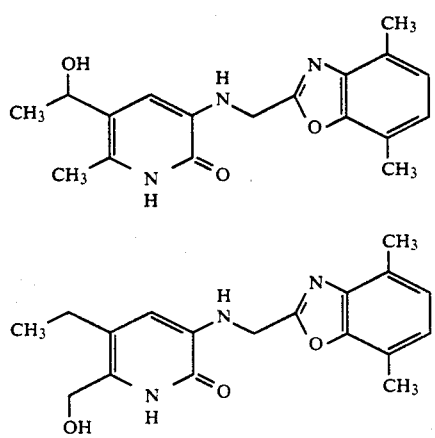

comprising incubation of compound (III), an inhibitor of the reverse transcriptase encoded by human immunodeficiency virus (HIV),

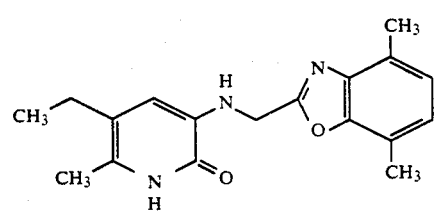

with a preparation from mammalian organ. Compounds (I) and (II) or the pharmaceutically acceptable salts thereof inhibit the reverse transcriptase encoded by HIV and are of value in the prevention of infection by HIV, the treatment of infection by HIV and the treatment of the resulting acquired immune deficiency syndrome (AIDS).

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

The compounds prepared by the process of this invention are inhibitors of HIV reverse transcriptase. Furthermore, the compounds of the present invention do not require bio-activation to be effective.

DETAILED DESCRIPTION OF THE INVENTION

The novel process of this invention comprises incubation of compound (III)

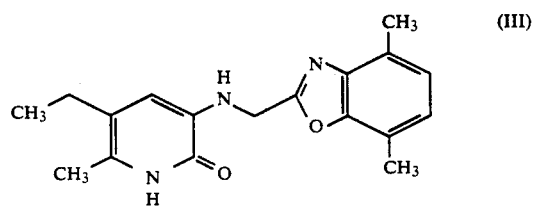

with a preparation from mammalian organ, and isolation of the resulting biotransformation products, compounds (I) and (II), in a conventional manner.

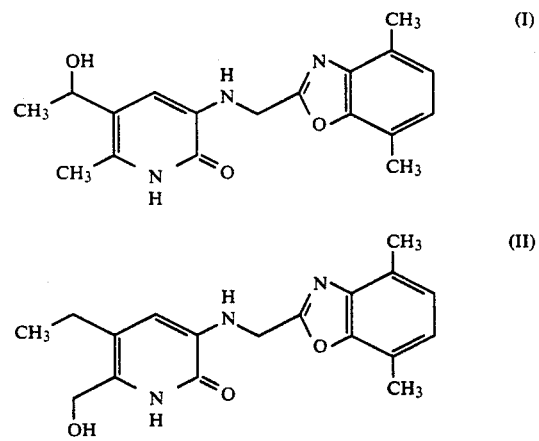

In general, compound (I), the 5-(1-hydroxy)-ethyl oxidation product, and compound (II), the 6-hydroxymethyl oxidation product, can be produced by incubating an appropriate amount of substrate compound (III) with certain mammalian tissues or cell cultures in an aqueous medium suitable for enhancing the viable life of the tissues or cells. Metabolites (I) and (II) may be produced by incubation of compound (III) with a preparation from mammalian organ containing: a) preparations from surgically derived specimens including liver, kidneys, lungs and skin, both from animals and human beings; b) prenatal and gestational tissues; c) cell cultures; d) subcellular fractions like microsomes, S9 and cytosol; and/or e) purified mixed function oxidases or flavin monooxygenases. These metabolites could also be formed in vivo in animals and human beings. The preferred tissue for production of compounds (I) and (II) is liver, especially rat liver slices.

The appropriate amount of tissue or cell culture to be used with a given amount of substrate compound will vary with the particular type of culture used. An appropriate ratio of substrate compound (III) to be incubated with liver tissue (mg:g, wet weight) ranges from about 1:0.3 to 1:3.0, preferably 1:2.4. When using surgically derived specimens, especially liver, the specimen is preferably cut into slices with thickness ranging from about $100\mu$ to $1000\mu$, and more preferably from about 250 to $400\mu$.

Aqueous media sufficient in amount and kind to keep the tissue or cells healthy in the incubation process should be used. These media are known and available in the art of drug metabolism and include various buffers and standard culture media with or without additives. A few examples of various culture media that may be employed are Williams' Medium E, Waymouth's Medium, Dulbecco's Medium, RPMI Medium and the like. Culture media could be replaced by general buffers like phosphate buffers, Krebs-Henseleit buffer, etc. Various additives that may be used to enhance the viable life of the cells and tissues are a) serum from bovine, horse, chicken, goat, sheep, rabbit and the like; b) HEPES or MOPS; c) gentamycin; and d) insulin, for example. A preferred medium for incubation of substrate compound (III) with rat liver slices is Williams' Medium E (composition described in Example 5 in this application).

The material is incubated at a temperature between 35° and 39° C., preferably 37° C., and at a pH between 7.2 and 7.6, preferably 7.4, under an atmosphere of 0% to 5% carbon dioxide in oxygen, or 100% air. The material is incubated for a period of time necessary to complete the oxidative biotransformation as monitored by HPLC (high performance liquid chromatography), usually for a period of about four hours when incubated with rat liver slices.

The biotransformation products (I) and (II) can be isolated and purified from the incubation mixture by extraction with a conventional solvent, such as methylene chloride, ethyl acetate, acetonitrile, methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred recovery method is solvent extraction, particularly using ethyl acetate. A preferred purification method involves the use of chromatography, especially HPLC, using a bonded silica gel column. Eluant mixtures for chromatography can be composed of water and an organic solvent such as methanol, acetonitrile and the like, and may optionally include a small amount of base, such as ammonium bicarbonate, or an acid, such as trifluroacetic acid or phosphoric acid. A preferred eluant is composed of acetonitrile and water containing 0.1% ammonium bicarbonate and is run through the column with a linear gradient.

Compounds (I) and (II) of the present invention are useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, accidental needle stick, exchange of body fluids, bites, or exposure to patient blood during surgery.

Reverse Transcriptase Assay

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C)•oligo d(G)$_{12-18}$. Compounds (I) and (II) inhibit this incorporation.

Thirty uL of a reaction mixture containing equal volumes of: 500 mM Tris•HCl (pH 8.2), 300 mM MgCl$_2$, 1200 mM KCl, 10 mM DTT, 400 $\mu$g/mL poly r(c)•oligo d(G) [prepared by dissolving 1.5 mg (25 U) poly r(C)•oligo d(G) in 1.5 ml sterile distilled H$_2$O and diluting to 400 $\mu$g/ml], 0.1 $\mu$Ci/$\mu$l [$^3$H] dGTP, 160 $\mu$M dGTP, were added to 10 $\mu$l sterile distilled H$_2$O, 2.5 $\mu$l of potential inhibitor. Ten $\mu$L of 3.2 nM purified HIV $RT_R$ were added to start the reaction. The mixture was incubated at 37° C. for 45 minutes.

After incubation was complete, the tubes were cooled in ice for 5 minutes. Ice-cold 13% TCA containing 10 mM NaPP$_i$ (200 $\mu$l) was added and the mixture incubated on ice for 30 minutes. The precipitated cDNA was removed by filtration using presoaked glass filters [TCA, NaPP$_i$]. The precipitate was then washed with 1N HCl, 10 mM NaPP$_i$. The filter discs were then counted in a scintillation counter.

Under these conditions [dGTP] and poly r(C)•oligo d(G)$_{12-18}$ each are approximately equal to the appropriate Km value. Approximately 5–6,000 cpm of [$^3$H] GMP are incorporated into acid-precipitable material. The RT reaction is concentration- and time-dependent. DMSO (up to 5%) does not affect enzyme activity.

Compounds (I) and (II) were evaluated using the methodology described above. The calculated IC$_{50}$ of compounds (I) and (II) were found to be about 405 nM and 33 nM, respectively, thereby demonstrating and confirming the utility of compounds (I) and (II) as effective HIV reverse transcriptase inhibitors.

The following examples are given for the purpose of illustrating the present invention and should not be construed as being limitations on the scope or spirit of the instant invention.

EXAMPLE 1

Preparation of Compound (III): 3-[(4,7-Dimethylbenzoxazol-2-yl)-methylamino]-5-ethyl-6-methyl-2(1H)-pyridinone Step A: Preparation of 3-amino-5-ethyl-6-methyl-2-(1H)-pyridinone Step 1: Preparation of 5-ethyl-6-methyl-3-nitro-2(1H)-pyridinone A mixture of 2-ethyl-3-oxobutanal, sodium salt (7.5 g, 55 mmol), nitroacetamide (6.6 g, 63 mmol), aqueous piperidinium acetate (4.4 mL) [prepared from glacial acetic acid (42 mL), water (100 mL) and piperidine (72 mL)] in water (45 mL) was stirred at room temperature for 22 hours. The yellow precipitate was collected by filtration and air dried to yield 5-ethyl-6-methyl-3-nitro-2-(1H)-pyidinone.

Step 2: Preparation of 3-amino-5-ethyl-6-methyl-2(1H)-pyridinone

A yellow solution of the 5-ethyl-6-methyl-3-nitro-2(1H)-pyridinone (10 g, 55 mmol) in a mixture of methanol and tetrahydrofuran (100 mL, 1:1 v/v) was reduced catalytically in the presence of 7% palladium on charcoal (0.7 g) under and atmosphere of hydrogen (50 psi) at room temperature over a period of 3.5 hours. The resultant mixture was filtered through a small pad of Celite. The filtrate was concentrated under reduced pressure (15 torr) to provide the corresponding aminopyridone.

Step B: Preparation of 2-chloromethyl-4,7-dimethylbenzoxazole

To a solution of 2,5-dimethyl-6-aminophenol (0.67 g, 4.9 mmol) in methylene chloride, solid ethyl 2-chloroiminoacetate hydrochloride (0.85 g, 4.9 mmol) was added. The resultant slurry was stirred at room temperature for 18 hours, then filtered through a plug of diatomaceous earth and concentrated under reduced pressure (15 torr). The solid residue was subjected to column chromatography on silica gel (50 g, eluted with 1% methanol in chloroform). Collection and concentration of appropriate fractions yielded the title benzoxazole.

Step C: Preparation of 3-[(4,7-dimethylbenzoxazol-2-yl)methylamino]-5-ethyl-6-methyl-2(1H)-pyridinone A mixture of 3-amino-5-ethyl-6-methyl-2-(1H)-pyridinone (0.23 g, 1.5 mmol), 2-chloromethyl-4,7-dimethylbenzoxazole (0.29 g, 1.5 mmol, diisopropylethylamine (0.39 g, 3 mmol) in acetonitrile (50 mL) was refluxed under an atomsphere of nitrogen for 12 hours. The resultant mixture was concentrated under reduced pressure (15 torr). The residue was then subjected to column chromatography on silica gel (100 g, elution with 4% methanol in chloroform). Collection and concentration of appropriate fractions provided the title compound.

Anal. Calcd for $C_{18}H_{21}N_3O_2$: C, 69.43; H, 6.80; N, 13.49. Found C, 69.32; H, 6.66; N, 13.47.

EXAMPLE 2

Biotransformation of Compound (III) by Rat Liver Slices

Compound (III) (16.06 μmol, 0.5 ml DMSO) was incubated for four hours with rat liver slices (12 g wet weight, 250–400 μ thick, ~1.2 cm wide) in 100 ml of Williams' Medium E (composition described in Sigma commercial circular, pages 1–5 and Example 5 of this application) at pH 7.4, 37° C. under an atmosphere of 95% oxygen and 5% carbon dioxide. The incubation mixture was extracted three times with one volume of ethyl acetate. Pooled organic extract was concentrated under vacuum, reconstituted in methanol, and subjected to high performance liquid chromatography (HPLC) on a $C_{18}$ column eluted with an acetonitrile-0.1% aqueous ammonium bicarbonate gradient. Effluents were monitored by a UV diode array detector at 215 nm and 325 nm.

Seven metabolites, M1, M6, M7, M8, M10, M10a and M10b, were characterized by $^1$H-NMR and/or FAB/-Mass spectrometry. Mass spectral measurements, by FAB/MS for M8 and M10 gave a protonated molecular ion at m/z 328 which showed the metabolites to be hydroxy derivatives of compound (III). The structures of interest were found to be as follows:

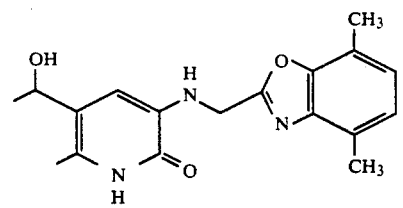

M8
COMPOUND (I)

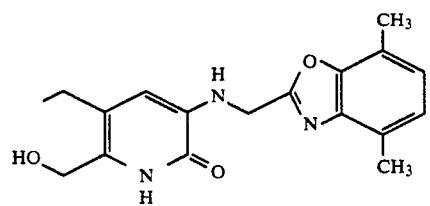

M10
COMPOUND (II)

Hydroxylation of C-1 of the ethyl side chain in compound (I) was evident from the appearance of the terminal methyl group as a doublet at 1.29 ppm (rather than a triplet at 1.06 ppm in parent compound (III)), and the appearance of a C$\underline{H}$OH quartet at 4.83 ppm instead of the methylene quartet at 2.34 ppm in the parent compound.

Hydroxylation of the 6-methyl group in compound (II) was indicated by the disappearance of the methyl singlet near 2.16 ppm of substrate compound (III) and the appearance instead of a new singlet at approximately 4.48 ppm ascribable to the C$\underline{H}_2$OH protons. The $^1$H-NMR peak shifts for compounds (I) and (II) are relative to acetone set at 2.05 ppm.

EXAMPLE 3

Composition of Williams' Medium E

Williams' Medium E (with L-glutamine and without sodium bicarbonate) is composed of:

| Component | g/L |
|---|---|
| L-Alanine | 0.090 |
| L-Arginine | 0.050 |
| L-Aspartic Acid | 0.030 |
| L-Asparagine.H$_2$O | 0.020 |
| L-Cysteine | 0.040 |
| L-Cystine | 0.020 |
| L-Glutamic Acid | 0.0445 |
| L-Glutamine | 0.292 |
| Glycine | 0.050 |
| L-Histidine Free Base | 0.015 |
| L-Isoleucine | 0.050 |
| L-Leucine | 0.075 |
| L-Lysine.HCl | 0.08746 |
| L-Methionine | 0.015 |
| L-Phenylalanine | 0.025 |
| L-Proline | 0.030 |
| L-Serine | 0.010 |
| L-Threonine | 0.040 |
| L-Tryptophan | 0.010 |
| L-Tyrosine 2Na | 0.05045 |
| L-Valine | 0.050 |
| Ascorbic Acid Na | 0.00227 |
| d-Biotin | 0.0005 |
| Choline Chloride | 0.0015 |
| Ergocalciferol | 0.0001 |
| Folic Acid | 0.001 |
| Glutathione | 0.00005 |
| myo Inositol | 0.002 |
| Menadione Sodium Bisulfite | 0.00001 |
| Linoleic Acid Methyl Ester | 0.00003 |

| Component | g/L |
| --- | --- |
| Niacinamide | 0.001 |
| Pyridoxal HCl | 0.001 |
| Riboflavin | 0.0001 |
| Pyruvic Acid Na | 0.025 |
| Thiamine HCl | 0.001 |
| Tocopherol Phosphoric Acid 2Na | 0.00001 |
| Vitamin A Acetate | 0.0001 |
| Vitamin B12 | 0.0002 |
| D-Pantothenic Acid Ca | 0.001 |
| Calcium Chloride 2H$_2$O | 0.265 |
| CuSO$_4$ .5H$_2$O | 0.0000001 |
| Fe[NO$_3$]$_3$9H$_2$O | 0.0000001 |
| MnCl$_2$.4H$_2$O | 0.0000001 |
| MgSO$_4$ Anhydrous | 0.0977 |
| Potassium Chloride | 0.400 |
| Sodium Chloride | 6.800 |
| NaH$_2$PO$_4$ Anhydrous | 0.122 |
| ZnSO$_4$.7H$_2$O | 0.0000002 |
| Phenol Red Na | 0.0107 |
| Glucose | 2.000 |

As used in Example 2, the above described medium was prepared with the addition of water and sodium bicarbonate, and the pH was adjusted to 7.4 with the addition of 1N HCl or 1N NaOH.

EXAMPLE 4

Organic Synthesis of Compound (II):
3-[(4,7-dimethylbenzoxazol-2-yl)methylamino]-5-ethyl-6-hydroxymethyl-2(1H)-pyridinone

Step A: Preparation of 3-nitro-5-ethyl-6-benzyloxymethyl-2(1H)-pyridinone

Benzyloxyacetylchloride (14.2 mL, 0.09 mol) in dry tetrahydrofuran (10 mL) was added dropwise to a solution of 1-(N-morpholino)-1-butene (12.8 g, 0.09 mol) and triethylamine (12.6 mL, 0.09 mol) in dry tetrahydrofuran (120 mL) warmed at 70° C. under a nitrogen atmosphere. After 1.25 hours, the reaction was cooled to room temperature and nitroacetamide ammonium salt (12.0 g, 0.099 mol) was added followed by the dropwise addition of acetic acid (11.4 mL, 0.20 mol). After stirring for 20-24 hours, the reaction was diluted with chloroform (150 mL) and the solution washed with water, 10% HCl, dried (Na$_2$SO$_4$) and filtered through a pad of charcoal. The solvent was removed and the residue triturated with cold methanol. The crystalline yellow product was filtered, rinsed with methanol and diethyl ether to give the title compound, mp 157°–158° C.

Anal. calcd. for C$_{15}$H$_{16}$N$_2$O$_4$: C, 62.49; H, 5.59; N, 9.72. Found: C, 62.11; H, 5.26; N, 9.68.

Step B: Preparation of 3-amino-5-ethyl-6-hydroxymethyl-2(1H)-pyridinone

A solution of 3-nitro-5-ethyl-6-benzyloxymethyl-2(1H)-pyridinone (576 mg, 2.0 mmol) in tetrahydrofuran (15 mL) and methanol (15 mL) containing 10% palladium/charcoal (130 mg) was hydrogenated at atomspheric pressure, monitoring the progress by thin layer chromatography (tlc). Additional catalyst was added in 100 mg portions after day 2 and day 3. After 3-4 days, the catalyst was filtered and the solvents evaporated. The catalyst was vigorously washed with methanol/chloroform and combined solvents evaporated. The residue was triturated with methylene chloride and product collected by filtration to give 136 mg of 90% pure product. This material was used without further purification.

Step C: Preparation of 3-[(4,7-dimethylbenzoxazol-2-yl)methylamino]-5-ethyl-6-hydroxymethyl-2(1H)-pyridinone Using substantially the same procedure as described in Example 1, Step C, but substituting 3-amino-5-ethyl-6-hydroxymethyl-2(1H)-pyridinone for the 3-amino-5-ethyl-6-methyl-2-(1H)-pyridinone used therein, the title compound is obtained.

EXAMPLE 5

Organic Synthesis of Compound (I):
3-[(4,7-dimethylbenzoxazol-2-yl)methylamino]-5-(1-hydroxyethyl)-6-methyl-2(1H)-pyridinone The title compound is obtained by employing susbstantially the some procedures as described in Example 1, with the following modifications.

1) The 2-ethyl-3-oxobutanal, sodium salt, used as a starting material in Step A, Step 1 is replaced by

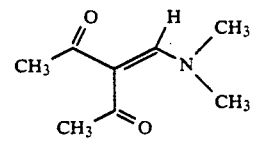

to obtain the intermediate 3-nitro-5-acetyl-6-methyl-2(1H)-pyridinone. 2) The 3-nitro-5-acetyl-6-methyl-2(1H)-pyridinone intermediate is next treated with sodium borohydride (approx. 1 molar equivalent) in ethanol at room temperature for a sufficient time to reduce the 5-acetyl group to a 5-(1-hydroxyethyl) group. The reaction mixtue is then treated with a small amount of acid, and the product is recovered and purified using standard methods.

3) The remaining procedures in Example 1, from Step A, Step 2, to the end, are substantially followed except that the 5-ethyl-6-methyl-3-nitro-2-(1H)-pyridinone and its intermediates used therein are replaced by 3-nitro-5-(1-hydroxyethyl)-6-methyl-2(1H)-pyridinone and its intermediate.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process for the preparation of a compound of structural formula (I) or (II)

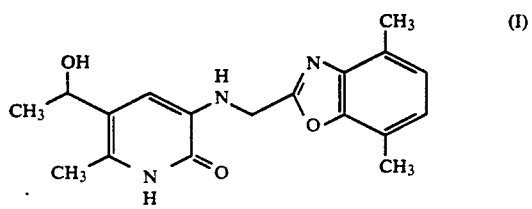

-continued

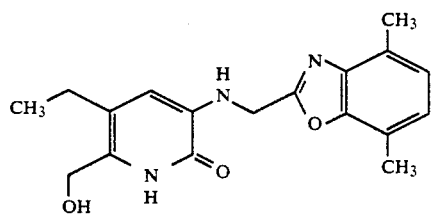
(II)

comprising the steps of:
a) providing a quantity of compound (III),

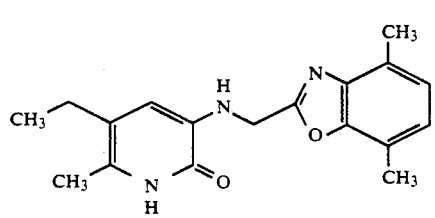
(III)

b) incubating the compound of Step (a) with a preparation from mammalian organ selected from the group consisting of liver and kidney under aerobic conditions and
c) isolating compounds (I) or (II) or both.

2. The process of claim 1 wherein the temperature is 35°-39° C. and the pH is 7.2-7.6.

3. The process of claim 2 wherein the temperature is 37° C. and the pH is 7.4.

4. A process for the preparation of a compound of structural formula (I) or (II)

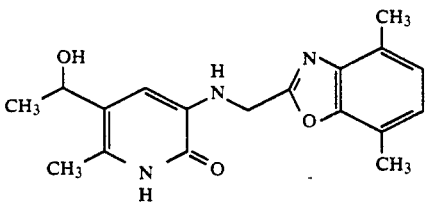
(I)

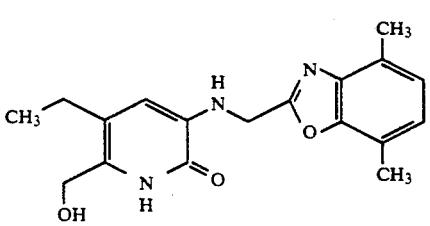
(II)

comprising the steps of:
a) providing a quantity of compound (III),

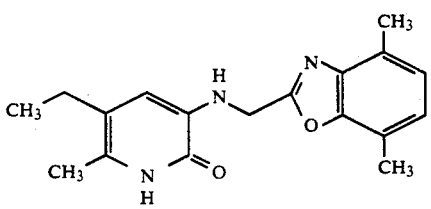
(III)

b) incubating the compound of Step (a) with a preparation from mammalian liver under aerobic conditions and
c) isolating compounds (I) or (II) or both.

5. The process of claim 4 wherein the preparation from mammalian organ is comprised of rat liver slices.

* * * * *